United States Patent [19]

Cummings et al.

[11] Patent Number: 4,744,951
[45] Date of Patent: May 17, 1988

[54] VAPORIZATION METHOD TO ENHANCE STERILANT PENETRATION

[75] Inventors: Arthur L. Cummings, Erie; Jack H. Young, Cambridge Springs; Ralph W. Makinen, Erie, all of Pa.

[73] Assignee: American Sterilizer Company, Erie, Pa.

[21] Appl. No.: 733,014

[22] Filed: May 10, 1985

Related U.S. Application Data

[63] Continuation-in-part of Ser. No. 548,956, Nov. 7, 1983, abandoned.

[51] Int. Cl.$^4$ ............................................. A61L 2/20
[52] U.S. Cl. ........................................ 422/28; 422/27
[58] Field of Search .................... 422/27, 28; 55/279; 430/973

[56] References Cited

U.S. PATENT DOCUMENTS

| | | | |
|---|---|---|---|
| 3,489,505 | 1/1970 | Schumann | 422/292 X |
| 3,490,863 | 1/1970 | Schumann et al. | 422/28 X |
| 3,687,612 | 8/1972 | Ernst | 422/27 |
| 3,904,361 | 9/1975 | Egger | 53/167 X |
| 3,908,031 | 9/1975 | Wistreich et al. | 422/27 X |
| 3,910,761 | 10/1975 | Hopkins | 422/108 |
| 4,169,123 | 9/1979 | Moore et al. | 422/28 X |
| 4,169,124 | 9/1979 | Forstrom et al. | 422/28 X |
| 4,230,663 | 10/1980 | Forstrom et al. | 422/28 X |
| 4,294,804 | 10/1981 | Baran . | |
| 4,366,125 | 12/1982 | Kodera et al. | 422/27 X |
| 4,380,530 | 4/1983 | Kaye | 422/300 |
| 4,410,492 | 10/1983 | Kaye | 422/27 |
| 4,424,189 | 1/1984 | Hick | 368/307 |
| 4,512,951 | 4/1985 | Koubek | 422/33 |

FOREIGN PATENT DOCUMENTS

| | | | |
|---|---|---|---|
| 3440714 | 6/1985 | Fed. Rep. of Germany | 422/28 |
| 221227 | 12/1984 | Japan | 422/28 |
| 1561495 | 2/1980 | United Kingdom . | |
| 1574488 | 9/1980 | United Kingdom . | |
| 1582060 | 12/1980 | United Kingdom . | |

OTHER PUBLICATIONS

Block, *Disinfection, Sterilization and Preservation*, Lea & Febiger, Philadelphia, Pa., (1977), pp. 677-684.

Primary Examiner—David L. Lacey
Assistant Examiner—Jill Johnston
Attorney, Agent, or Firm—Kirkpatrick & Lockhart

[57] ABSTRACT

A process for concentrating hydrogen peroxide from a relatively dilute solution of hydrogen peroxide and water and supplying the concentrated hydrogen peroxide in vapor form to a sterilization chamber. The process includes vaporizing a major portion of the water from the solution and removing the water vapor thereby produced before injecting the concentrated hydrogen peroxide vapor into the sterilizing chamber.

3 Claims, 1 Drawing Sheet

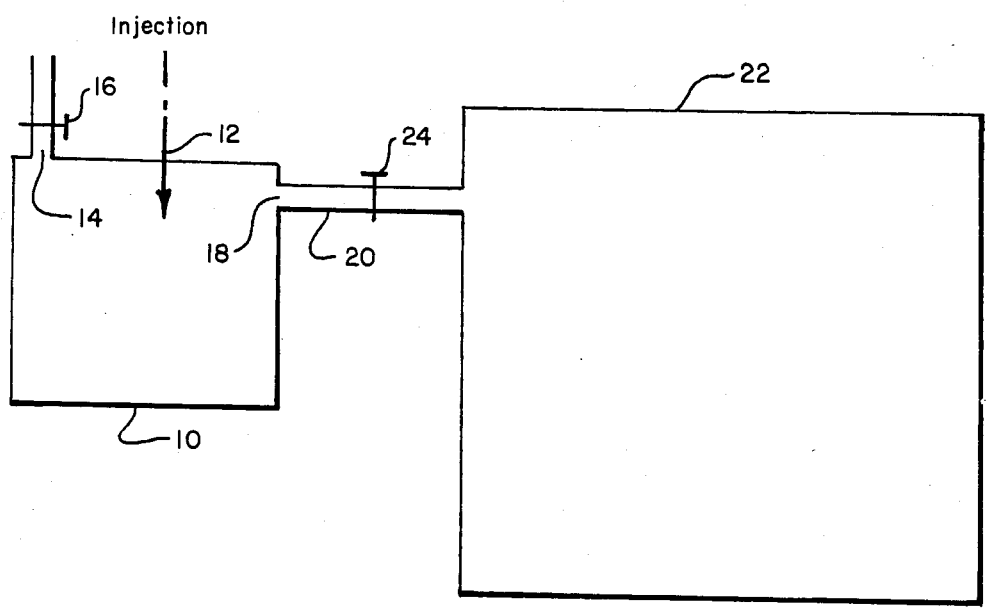

VAPORIZATION METHOD TO ENHANCE STERILANT PENETRATION

CROSS REFERENCE TO RELATED APPLICATION

This is a continuation-in-part of U.S. application Ser. No. 548,956, filed Nov. 7, 1983.

BACKGROUND OF THE INVENTION

1. Field of the Invention

This invention relates to a process for concentrating a solution of hydrogen peroxide and water and furnishing vapors of said concentrated solution to a sterilization chamber containing goods that require sterilant penetration to be sterilized.

2. Description of the Prior Art

U.S. Pat. Nos. 4,169,123 and 4,169,124 to Moore et al. and Forstrom et al., respectively, (hereinafter referred to collectively as "Moore and Forstrom") teach that gaseous hydrogen peroxide can be an effective sterilant and may be employed in a relatively "cold" sterilization process (that is, in the same general temperature range as that used, for example, in ethylene oxide sterilization processes) without the attendant disadvantages of known cold sterilization processes. Moore and Forstrom implement their gaseous hydrogen peroxide sterilization process by vaporizing in a closed sterilization chamber a relatively dilute liquid solution of hydrogen peroxide and water (in the range of 0.05 to 5% by weight hydrogen peroxide) and permitting the vapors so produced to contact items to be sterilized, which are located within the sterilization chamber, until sterilization is achieved.

Moore and Forstrom claim that sterilization may be effected by their process at remarkably low concentrations (on the order of 0.5 mg/liter) of hydrogen peroxide. Since hydrogen peroxide vapor, not water vapor, is the sterilizing agent in the Moore and Forstrom process, it may be seen that the effective concentration of sterilizing agent at the point of attack on the object to be sterilized would be relatively lower, due to the presence of water vapor, than a situation in which pure hydrogen peroxide vapor were present. That is, a given weight of hydrogen peroxide in liquid solution can produce only that weight of hydrogen peroxide in vapor form assuming complete vaporization. Clearly, therefore, it would be preferable to use highly concentrated hydrogen peroxide as the starting material in a gaseous hydrogen peroxide sterilization process. The handling requirements, however, for highly concentrated hydrogen peroxide solution (say above about 65% by weight) are so onerous because of the hazard posed by such a strong oxidant that the use of such highly concentrated solutions is impractical.

Moore and Forstrom are silent on the desirability of increasing the effective concentration of hydrogen peroxide vapor at the point of attack. They are also silent on a problem experienced in the application of their process when the nature of the goods to be sterilized requires that sterilant penetrate wrapping material and/or long, small-diameter tubes (lumens) such as are present on endoscopes. Indeed, this requirement for sterilant penetration is often present with heat-sensitive goods that may not be subjected to steam sterilization and thus require "cold" sterilization. The problem discovered with the Moore and Forstrom process where sterilant penetration is needed centers around the well-known difference in volatility and sonic velocity between water and hydrogen peroxide; specifically, water is more volatile than hydrogen peroxide and vaporizes first; further water vapor has a higher translational and sonic velocity than hydrogen peroxide vapor and thus a higher diffusion rate in air than hydrogen peroxide vapor. If, for example, a solution of hydrogen peroxide and water is injected into an evacuated sterilization chamber, the more volatile, faster-traveling water vapor penetrates tubes and wraps; once at these locations, the water vapor forms a barrier to penetration of the less volatile, slower-traveling hydrogen peroxide vapor. Accordingly, the effective concentration of hydrogen peroxide vapor at the point of attack is diminished. Alternatively, if the liquid solution of hydrogen peroxide and water could be vaporized and the vapor homogenized prior to injection into the sterilization chamber, the procedure also would be unsuccessful from the standpoint of effective concentration of hydrogen peroxide vapor at the point of attack. First, water vapor dominates the vapor phase over a hydrogen peroxide-water solution such that, for example, an 18.5 mole % hydrogen peroxide liquid supports a vapor containing only 1.0 mole % hydrogen peroxide at room temperature. Such a relatively weak mixture of peroxide is an ineffective sterilant for narrow lumens. Second, the combination of the relative concentrations, sonic velocities and translational velocities of the two gases would tend to cause water vapor to penetrate narrow lumens ahead of the hydrogen peroxide vapor.

The foregoing establishes that the teachings of Moore and Forstrom fall far short of producing effective concentrations of hydrogen peroxide vapor at the point of attack where penetration of the vapor into wraps and narrow lumens is required. There exists, therefore, a need for a process that will enhance the concentration of hydrogen peroxide vapor at the point of attack with goods in the sterilizer that require the sterilant to traverse tortuous paths, such as wrapped goods, and penetrate narrow lumens.

SUMMARY OF THE INVENTION

The present invention provides a process for concentrating a solution of hydrogen peroxide and water and supplying concentrated hydrogen peroxide in vapor form to a sterilization chamber containing goods that require sterilant penetration to be sterilized. The process comprises the steps of injecting a predetermined amount of a relatively dilute solution of hydrogen peroxide and water into an evacuated vaporization chamber; vaporizing (or flashing) a major portion of the water from the solution and withdrawing the water vapor thereby produced from the vaporization chamber; and vaporizing the remaining portion of the solution, now concentrated to greater than 40%, preferably in the range of 50 to 80%, hydrogen peroxide by weight, and conveying the vapors of the remaining portion to an evacuated sterilization chamber. The term "relatively dilute" in referring to a hydrogen peroxide/water solution means 30% by weight hydrogen peroxide or less.

Other details and advantages of the present invention will become apparent as the following detailed description, taken with the accompanying drawing, proceeds.

BRIEF DESCRIPTION OF THE DRAWINGS

The FIGURE is a diagrammatic view of apparatus for use in carrying out the present invention.

DETAILED DESCRIPTION OF THE PREFERRED EMBODIMENTS

Referring to the single FIGURE, there is shown in diagrammatic form apparatus for use in carrying out the process of the present invention. The apparatus includes a vaporizing chamber 10 having any well-known means 12 for injecting into chamber 10 a predetermined amount of a solution of hydrogen peroxide and water. Chamber 10 may be controllably heated by any well-known means. Chamber 10 has an outlet port 14 through which vapors may be exhausted from chamber 10 by means of a vacuum. Port 14 may be opened or closed by valve 16. Chamber 10 also has an outlet port 18 leading through passage 20 to a sterilization chamber 22. Passage 20 may be open or closed by valve 24.

In the practice of the present invention, valve 24 is closed and valve 16 is open; vacuum is applied to chamber 10 to evacuate air. Chamber 10 is heated until the desired temperature within chamber 10 is reached; that temperature is such that, when taken with the pressure within chamber 10, water in the form of vapor will be flashed from a solution of liquid hydrogen peroxide and water present in chamber 10.

The process of the present invention then is initiated by the injection into evacuated chamber 10 of predetermined amount of a liquid solution of hydrogen peroxide and water through injection means 12. Conditions within chamber 10 cause the preferential vaporization of water from the solution and the vapor formed thereby is withdrawn from chamber 10 through port 14. At a point in time when a major portion of the water in the injected solution has been vaporized and withdrawn, but before a significant quantity of hydrogen peroxide has vaporized and been withdrawn, valve 16 is closed. What remains in chamber 10 is a hydrogen peroxide-water solution enriched in hydrogen peroxide, specifically greater than 40% hydrogen peroxide by weight, preferably 50 to 80% by weight. Vaporization of this enriched solution continues within chamber 10 and then valve 24 is opened to admit the vapors formed thereby to evacuated sterilization chamber 22. With a substantial amount of the water having been removed, the hydrogen peroxide vapor sterilant is able to disperse itself throughout the sterilizer and penetrate wraps and tubes without encountering a barrier effect that otherwise would have been present by reason of the effects of the present of water discussed above. Thus, the effective concentration of hydrogen peroxide vapor at the point of attack on the goods to be sterilized is markedly enhanced by the process of the invention.

The following are nonlimiting examples of the practice of the present invention:

EXAMPLES

The equipment used in Examples 1 and 2 described below includes a vaporization chamber 10 having a volume of 1.7 liters and being heated to provide a temperature of 90° C. within the chamber. Sterilization chamber 22 is conventional and has a volume of 20.6 liters. The pressure and temperature maintained within sterilization chamber 22 are 0.01 atmospheres and 55° C., respectively. The injected solution in Examples 1 and 2 is 1 ml of a 30 weight percent (18.5 mole %) solution of hydrogen peroxide and water. The procedure used in Examples 1 and 2 is that described above, except that in one instance valve 16 is not opened at all in order to illustrate the adverse effect of the presence of water vapor in the sterilization chamber 22.

EXAMPLE 1

The goods to be sterilized are stainless steel tubes, 32 cm in length, an outside diameter of ¼ inch, an inside diameter of 5 mm, and having an enlarged chamber at the center. A spore carrier consisting of *Bacillus subtilis* innoculated on peni cylinders, which are prepared and validated in accordance with AOAC Operating Technique 4.017, is placed in the enlarged chamber of each tube. During the procedure, valve 16 remains open for 5 seconds.

EXAMPLE 2

The procedure was identical to that of Example 1 except that valve 16 was not opened at all.

The sterilization data for Examples 1 and 2 are presented below in Table I.

TABLE I

| Example No. | Weight Percent Hydrogen Peroxide Delivered to Sterilizer | Spore Kill |
| --- | --- | --- |
| 1 | >40 | 8 of 8 sterile |
| 2 | 30 | 2 of 2 not sterile |

In Examples 3-5 described below, the objects to be tested for sterilant penetration are glass tubes having an inside diameter of 2 mm and a length of 32 cm. The extent of penetration of hydrogen peroxide into a tube is measured by colorimetrically assaying the amount of hydrogen peroxide deposited on a strip of filter paper which is placed inside the tube at its center. The assay is accomplished by extracting the absorbed hydrogen peroxide from the strip with water. The extraction proceeds by soaking the strip in one milliliter of water for at least 30 minutes. The peroxide in an aliquot of the extract is determined by reaction with ferrous ammonium sulfate in the presence of acid and the dye xylenol orange. The optical absorbance of the resulting solution is measured at 525 nm and compared to the absorbance of solutions of known hydrogen peroxide content.

In Examples 3-5 reagent grade hydrogen peroxide aqueous solutions of varying concentrations are injected into a vaporizing chamber to permit the liquid to vaporize; then the vapors are allowed to travel into an evacuated sterilizing chamber containing the sample tubes.

In Example 3, 90% hydrogen peroxide, 10% water (by weight) is injected. Example 3 is considered to be a close approximation of the results achieved by the process of the present invention. In Example 4, 30% hydrogen peroxide, 70% water is injected. Example 4 is considered to be a simulation of Moore and Forstrom. In Example 5, an injection of water precedes an injection of 90% hydrogen peroxide solution. The purpose of Example 5 is to assure that water vapor reaches the sample tube before the hydrogen peroxide is injected. In each of the three tests, 158 mg. of hydrogen peroxide is injected.

The results of the tests are reported below in Table II:

TABLE II

| Example No. | Sterilant Penetration | | |
|---|---|---|---|
| | Injection | Total HP Injected, mg | HP Found At Tube Center, μg |
| 3 | 0.125 mL 90% HP* | 158 | 71 + 12 |
| 4 | 0.47 mL 30% HP | 158 | 29 + 8 |
| 5 | 0.342 mL water + 0.125 mL 90% HP | 158 | 35 + 11 |

*Hydrogen peroxide

Examples 3-5 establish that the phenomenon of preferential vaporization of water before hydrogen peroxide results in water vapor reaching and penetrating the sample tube first, there to form a barrier against penetration by hydrogen peroxide vapor when it arrives at the mouths of the tube. This conclusion is demonstrated by the results of Examples 4 and 5. When, however, as in Example 3, water vapor is substantially removed from the hydrogen peroxide solution in order to concentrate the solution to greater than 40% by weight hydrogen peroxide before the hydrogen peroxide vapor is introduced into the sterilization chamber, the impediment to penetration of the sterilant into the sample tube is removed, thereby permitting effective sterilization.

What is claimed is:

1. A process for furnishing concentrated hydrogen peroxide vapor to interior surfaces of articles having a tortuous or a narrow path, said articles being so disposed within an evacuated sterilization chamber so that said interior surfaces can be contacted by vapor only after it traverses said tortuous or narrow path, comprising the steps of:

heating a liquid solution of relatively dilute hydrogen peroxide and water within an evacuated first chamber to preferentially vaporize said water;

withdrawing a portion of said water vapor from said first chamber to concentrate said hydrogen peroxide remaining in said first chamber;

terminating said withdrawal of water vapor from said first chamber when said remaining hydrogen peroxide is sufficiently concentrated so as to produce, upon complete vaporization, vapors concentrated in hydrogen peroxide to greater than about 40% by weight;

continuing heating said liquid solution to completely vaporize said solution; and introducing into said sterilization chamber said vapors concentrated in hydrogen peroxide and maintaining said hydrogen peroxide vapors in contact with said articles until sterilization is achieved.

2. The process of claim 1 wherein:
said vapors introduced into said sterilization chamber are concentrated in hydrogen peroxide in the range of 50 to 80% by weight.

3. A process for sterilizing interior surfaces of articles having narrow or tortuous paths, said articles being so disposed within an evacuated sterilization chamber so that said interior surfaces can be contacted by vapor only after the vapor traverses said tortuous or narrow path, comprising the steps of:

substantially completely vaporizing a hydrogen peroxide liquid solution so as to produce vapors concentrated in hydrogen peroxide to greater than about 40% by weight;

introducing into said sterilization chamber said vapors concentrated in hydrogen peroxide; and maintaining said hydrogen peroxide vapors in contact with said articles until sterilization is achieved.

* * * * *

UNITED STATES PATENT AND TRADEMARK OFFICE
CERTIFICATE OF CORRECTION

PATENT NO. : 4,744,951

DATED : May 17, 1988

INVENTOR(S) : Arthur L. Cummings et al.

It is certified that error appears in the above-identified patent and that said Letters Patent is hereby corrected as shown below:

Col. 3, line 52, delete "present" and susbtitute therefore --presence--.

Signed and Sealed this

Fourteenth Day of March, 1989

Attest:

DONALD J. QUIGG

Attesting Officer

Commissioner of Patents and Trademarks